United States Patent [19]

Wehinger et al.

[11] Patent Number: 4,705,794
[45] Date of Patent: * Nov. 10, 1987

[54] ISCHAEMIA OR HYPOXIA CONTROLLING COMPOSITIONS CONTAINING PYRIDINECARBOXYLIC ACID ESTERS

[75] Inventors: Egbert Wehinger; Horst Meyer, both of Wuppertal; Ulrich Benz, Duesseldorf, all of Fed. Rep. of Germany

[73] Assignee: Bayer Aktiengesellschaft, Leverkusen, Fed. Rep. of Germany

[ * ] Notice: The portion of the term of this patent subsequent to Feb. 5, 2002 has been disclaimed.

[21] Appl. No.: 470,886

[22] Filed: Feb. 28, 1983

[30] Foreign Application Priority Data

Mar. 13, 1982 [DE] Fed. Rep. of Germany ....... 3209274

[51] Int. Cl.⁴ ................. A61K 31/455; C07D 213/00; C07D 401/04; C07D 491/048
[52] U.S. Cl. ..................................... 514/302; 514/334; 514/356; 546/258; 546/257; 546/116; 546/321; 546/271; 546/281; 546/283; 544/238; 544/333; 544/405
[58] Field of Search ............... 546/321, 280, 284, 273, 546/283, 271, 281, 270, 279, 167, 278, 139, 275, 144, 277, 116, 258; 544/238, 284, 333, 353, 405; 424/266, 258, 250, 251; 514/356, 334, 302

[56] References Cited

U.S. PATENT DOCUMENTS 4,497,821 2/1985 Wehinger et al. .................. 514/302
4,532,248 7/1985 Franckowiak et al. ............. 514/89

FOREIGN PATENT DOCUMENTS 5275164 6/1966 Australia .

OTHER PUBLICATIONS

Meyer, et al., "Nimodipine: Synthesis and Metabolic Pathway", Arzneim-Forsch. (Jan. 1983), vol. 33, pp. 106–111.
Shibanuma, et al., "Synthesis of the Metabolites of Nicardipine Hydrochloride", Chem. Pharm. Bull. (Sep. 1980), vol. 28, pp. 2609–2613.
Higuchi, et al (II), "Absorption, Excretion and Metabolism of a New Dihydropyridine", Xenobiotica, vol. 17, No. 8 (1977), pp. 469–479.
Higuchi, et al (III), "Metabolic Rate of Nicardipine Hydrochloride", Xenobiotica, vol. 10, No. 12 (1980), pp. 889–896.
Bossert, et al, "4-Aryldihydropyridines", Angew. Chem. Int. Ed. Engl. 20, 762–769 (1981).
Dzhemilev, et al, Chemical Abstracts 89:43046z (1978).
Angelova, et al., Chemical Abstracts 96:162501y (pub. 1981).
V. A. Petrow, J. Chem. Socl. 1946, pp. 884 to 888, H. Higushi et al, 95th General Congress of the Japanese Pharmaceutical Society, Apr. 1975.
S. E. Parker and J. Weinstock, Journal of Medicinal Chem. 1973, No. 1, pp. 34 to 37.
P. M. Carbateas and G. L. Williams J. Heterocyclic Chem. 11, 1974, pp. 819–821.
H. Medenwald, K. Schlossmann and C. Wünsche, Arzneim-Forsch., vol. 22, No. 1, 1972, pp. 53–56.

*Primary Examiner*—Henry R. Jiles
*Assistant Examiner*—Dale A. Bjorkman
*Attorney, Agent, or Firm*—Sprung, Horn, Kramer & Woods

[57] ABSTRACT

Pyridinecarboxylic acid esters of the formula

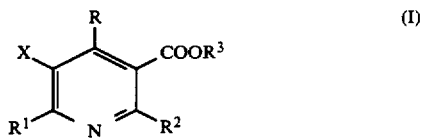

(I)

in which
R is an optionally substituted aryl or heterocyclic radical,
$R^1$ and $R^2$ are hydrogen, alkyl, aryl, aralkyl, acyloxyalkyl or hydroxyalkyl, or $R^1$ with X forms a carbonyl-containing heterocyclic ring,
X is —CN, —CO—$R^4$, —COO$R^5$ or —SO$_2R^6$,
$R^4$, $R^5$ and $R^6$ are various optionally substituted radicals, and
$R^3$ is different from $R^5$ and is a substituted-or interrupted-hydrocarbon radical,
or pharmaceutically acceptable salts thereof control the otherwise negative effects of ischaemia and/or hypoxia.

12 Claims, No Drawings

ISCHAEMIA OR HYPOXIA CONTROLLING COMPOSITIONS CONTAINING PYRIDINECARBOXYLIC ACID ESTERS

The present invention relates to new pyridine-carboxylic acid esters several processes for their preparation and their use in medicaments, in particular in agents for disorders which are due to ischaemia and/or hypoxia.

It has already been disclosed that diethyl 2,6-dimethyl-4-(2-nitrophenyl)pyridine-3,5-dicarboxylate is obtained by chromic acid oxidation of the corresponding diethyl 1,4-dihydro-2,6-dimethyl-4-(2-nitrophenyl)pyridine-3,5-dicarboxylate (see V. A. Petrow, J. Chem. Soc. 884 (1946)).

Furthermore, it has been disclosed that, during the biotransformation of 4-aryl-1,4-dihydropyridine derivatives having vasodilator activity, pyridines are produced which are significantly less vasoactive than the corresponding dihydropyridine compounds (see S. Higuchi et al. 95th General Congress of the Japanese Pharmaceutical Society, April 1975; S. E. Parker and J. Weinstock, J. Med. Chem. 16, 34 (1973); H. Medenwald, K. Schlossmann and C. Wünsche, Arzneim.-Forsch. 22, 53 (1972)).

Furthermore, it has been disclosed that the compound isopropyl 2-methoxyethyl 1,4-dihydro-2,6-dimethyl-4-(3-nitrophenyl)pyridine-3,5-dicarboxylate markedly improves experimentally induced disturbances of learning and memory (compare U.S. application Ser. No. 346,319 filed Feb. 5, 1982, now pending.)

Furthermore, 4-(3-nitrophenyl)pyridine-3,5-dicarboxylic acid esters have been used as intermediate products in the synthesis of pyridylquinolones having antibacterial activity (P. M. Carbateas and G. L. Williams, J. Heterocyclic Chem. 11, 819, (1974)).

The present invention relates to new pyridine-carboxylic acid esters of the general formula (I)

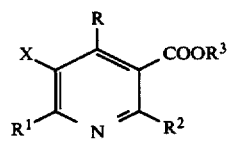

(I)

in which
R represents an aryl radical or represents a thienyl, furyl, pyrryl, pyrazolyl, imidazolyl, oxazolyl, isoxazolyl, thiazolyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl radical, the aryl radical and the heterocycles optionally containing 1 to 2 identical or different substituents from the group comprising phenyl, alkyl, alkoxy, alkylene, dioxyalkylene, halogen, trifluoromethyl, polyfluoroalkoxy, nitro, cyano, azido or $SO_m$-alkyl (m=0 to 2),
$R^1$ represents hydrogen, a straight-chain or branched alkyl radical, an aryl radical or an aralkyl radical, an acyloxyalkyl group, a hydroxyalkyl group or represents an alkylene chain which, together with X, forms a 5- to 7-membered ring which contains a carbonyl group and optionally an oxygen or a nitrogen atom,
$R^2$ represents hydrogen, a straight-chain or branched alkyl radical, an aryl radical or an aralkyl radical, or denotes an acyloxyalkyl or a hydroxyalkyl group,
X represents the nitrile group or represents the radical $—CO—R^4$, $R^4$ representing a straight-chain, branched or cyclic alkyl radical, an aryl radical or an aralkyl radical, or
X represents the group $—COOR^5$, $R^5$ representing a straight-chain, branched or cyclic, saturated or unsaturated hydrocarbon radical, which is optionally interrupted by 1 oxygen atom in the chain and/or is optionally substituted by halogen, cyano, hydroxyl, acyloxy, pyridyl, aryl or aryloxy, it being possible for the aryl groups in turn to be substituted by alkyl, fluorinated alkyl, alkoxy, halogen or nitro or by an amino group, which is optionally substituted by two identical or different substituents from the group comprising alkyl, aryl or aralkyl, or it being possible for $R^5$ also to be hydrogen, when $R^1$ represents a hydroxyalkyl or acyloxyalkyl group, or
X represents the group $—SO_2R^6$, $R^6$ representing a lower alkyl radical or a phenyl radical which is optionally substituted by halogen, trifluoromethyl, alkoxy or alkyl, and
$R^3$ is always different from $R^5$, and represents a straight-chain hydrocarbon radical, which is interrupted by an oxygen atom in the chain and/or is substituted by halogen, cyano, hydroxyl, acyloxy, dialkylamino, pyridyl, aryl or aryloxy, it being possible for the aryl groups in turn to be substituted by alkyl, fluorinated alkyl, alkoxy, halogen or nitro, and their pharmaceutically acceptable salts.

Surprisingly, the compounds according to the invention exhibits a strong protective effect against hypoxia, which is manifested both in hypoxia-induced amnesia and also in the tolerance to hopoxia. These specific pharmacological effects could not be expected from the state of the art. The new compounds according to the invention are an enrichment of pharmacy on the basis of these properties.

Furthermore, it has been found that the compounds of the formula (I) according to the invention are obtained by (A) reacting 1,4-dihydropyridine derivatives of the general formula (II)

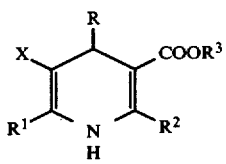

(II)

in which

R, $R^1$, $R^2$, $R^3$ and X have the meaning indicated above, with oxidizing (dehydrogenating) agents, optionally in the presence of inert solvents, at temperatures between 020 and 200° C., or (B) esterifying pyridinecarboxylic acids of the general formula (III)

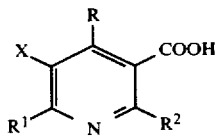

(III)

in which

R, R¹, R² and X have the meaning indicated above, optionally after activation of the carboxyl group in accordance with methods known from the literature, to give carboxylic acid esters of the general formula (I), or (C) in the case where R¹ and/or R² in the general formula (I) represent a hydroxyalkyl group, subjecting the corresponding monoacetoxyalkylpyridines or bisacetoxyalkylpyridines to the conditions of mild and selective hydrolysis, or (D) in the case where X in the formula (I) denotes carboxyl and R¹ denotes hydroxyalkyl, hydrolyzing compounds of the formula (IV)

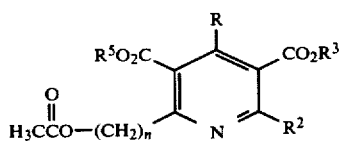

(IV)

in which

R, R², R³, R⁵ and n have the meaning indicated above, in the presence of alkali to give compounds of the formula (V), or (E) in the case where R¹ and X in the general formula (I) form a lactone ring, cyclizing hydroxyalkylpyridinecarboxylic acids of the general formula (V)

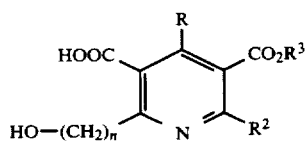

(V)

in which

R, R² and R³ have the meaning indicated above and n represents a number from 1 to 4, under the action of protons, by customary methods, to give compounds of the formula (VI)

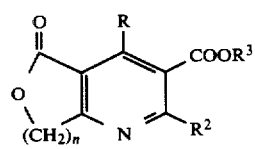

(VI)

in which

R, R², R³ and n have the meaning indicated above.

Compounds of the general formula (I) are of particular interest

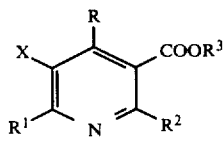

(I)

in which

R represents a phenyl or naphthyl radical or represents a thienyl, furyl, pyrryl, pyrazolyl, imidazolyl, oxazolyl, isoxazolyl, thiazolyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl radical, the phenyl or naphthyl ring and the heterocycles optionally containing 1 to 2 identical or different substituents from the group comprising phenyl, straight-chain or branched alkyl having 1 to 8 carbon atoms, cycloalkyl having 3 to 7 carbon atoms, alkoxy having 1 to 4 carbon atoms, trimethylene, tetramethylene or pentamethylene, dioxymethylene, dioxyethylene, fluorine, chlorine, bromine or iodine, trifluoromethyl, trifluoromethoxy, difluoromethoxy, tetrafluoroethoxy, nitro, cyano, azido or $SO_m$-alkyl, wherein m denotes a number from 0 to 2 and alkyl 1 to 4 carbon atoms, $R^1$ represents hydrogen or represents a straight-chain or branched alkyl radical having 1 to 8 carbon atoms, or represents the phenyl group, or represents the benzyl group or represents an acyloxyalkyl group having up to 6 C atoms, or represents a hydroxyalkyl group having up to 4 C atoms or represents an alkylene chain having 1 to 3 carbon atoms, which is optionally substituted by alkyl (1–4 C atoms) and which, together with X, forms a 5- to 7-membered ring, which contains as ring member a carbonyl group and, optionally, an oxygen or a nitrogen atom, the nitrogen optionally still carrying a hydrogen or a lower alkyl radical (1–4 C atoms), $R^2$ represents hydrogen or represents a straight-chain or branched alkyl radical having 1 to 8 carbon atoms or represents the phenyl group or represents the benzyl group or represents an acyloxyalkyl group having up to 6 C atoms or represents a hydroxyalkyl group having 1 to 4 C atoms, X represents the nitrile group or represents the radical $—COR^4$, $R^4$ representing a straight-chain, branched or cyclic alkyl radical having 1 to 8 carbon atoms, or the phenyl group or the benzyl group, or X represents the group $—COOR^5$, $R^5$ representing a straight-chain, branched or cyclic, saturated or unsaturated hydrocarbon radical having up to 12 carbon atoms which is optionally interrupted by 1 oxygen atom in the chain and/or is optionally substituted by halogen, cyano, hydroxyl, acyloxy, α-, β- or γ-pyridyl, phenyl, phenoxy or naphthoxy, it being possible for the aryl groups in turn to by substituted by lower alkyl (1–4 C atoms), trifluoromethyl, lower alkoxy (1–4 C atoms), fluorine or chlorine or nitro, or by an amino group which is optionally substituted by two identical or different substitutents from the group comprising alkyl having 1 to 2 carbon atoms, phenyl or benzyl, or it being possible for $R^5$ also to be hydrogen when $R^1$ represents a hydroxyalkyl or acyloxyalkyl group, or X represents the group —SO₂R⁶, R⁶ representing a lower alkyl radical having 1 to 8 carbon atoms, or a phenyl group which is optionally substituted by halogen, trifluoromethyl, alkyl or alkoxy, each having 1 to 4 carbon atoms, R³ is always different from R⁵ and represents a straight-chain hydrocarbon radical having up to 12 carbon atoms which is interrupted by an oxygen atom in the chain and/or is substituted by halogen, cyano, hydroxyl, acyloxy having up to 4 C atoms, dialkylamino having up to 6 carbon atoms per alkyl group, α-, β- or γ-pyridyl, phenyl or phenoxy, it being possible for the aryl groups in turn to be substituted by lower alkyl (1–4 C atoms), trifluoromethyl, lower alkoxy (1–4 C atoms), halogen or nitro, and their pharmaceutically acceptable salts.

Particular attention is drawn to compounds of the general formula (I) in which

R represents a phenyl or pyridyl radical, the phenyl radical optionally being substituted once or twice by nitro, cyano, trifluoromethyl, fluorine, chlorine, bromine, alkyl, alkoxy or alkylmercapto, each having 1 to 4 carbon atoms in the alkyl and alkoxy radicals, R¹ represents hydrogen or an alkyl radical having 1 to 4 carbon atoms, the phenyl group, the benzyl group, the acetoxymethyl group, the 2-acetoxyethyl group or a hydroxyalkyl group haveing 1 to 4 carbon atoms, or R¹, together with X, forms a 5- to 7-membered ring which contains as ring member a carbonyl group and optionally an oxygen or nitrogen atom, the nitrogen optionally still carrying a hydrogen atom or a lower alkyl radical having 1 to 4 C atoms, R² represents hydrogen or represents a straight-chain or branched alkyl radical having 1 to 4 carbon atoms, phenyl, benzyl, acetoxymethyl, 2-acetoxyethyl or hydroxyalkyl having 1 to 4 carbon atoms, X represents a nitrile group or X represents the radical —COR⁴, R⁴ representing a straight-chain or branched alkyl radical having 1 to 4 carbon atoms, phenyl or benzyl, or X represents the group —COOR⁵, R⁵ representing a straight-chain, branched or cyclic, saturated or unsaturated hydrocarbon radical having up to 10 carbon atoms which is optionally interrupted by an oxygen atom in the chain an/or is optionally substituted by fluorine, chlorine, bromine, cyano, hydroxyl, acetoxy, α-, β- or γ-pyridyl, phenyl or phenoxy, the aryl groups in turn being substituted by fluorine, chlorine, nitro, trifluoromethyl, alkyl or alkoxy each having 1 to 4 carbon atoms, or amino, the amino group in turn optionally being substituted by 2 identical or different substituents from the group comprising alkyl having 1 to 4 carbon atoms, phenyl or benzyl, or it being possible for R⁵ also to be hydrogen when R¹ represents a hydroxyalkyl or acyloxyalkyl group, or X represents the group —SO₂R⁶, R⁶ representing an alkyl radical having 1 to 4 carbon atoms or phenyl which is optionally substituted by fluorine, chlorine, trifluoromethyl, or alkyl or alkoxy each having 1 to 2 carbon atoms, R³ is always different from R⁵ and represents a straight-chain hydrocarbon radical having up to 6 carbon atoms which is interrupted by an oxygen atom in the chain and/or is substituted by fluorine, chlorine, bromine, cyano, hydroxyl, acetoxy, dialkylamino having up to 4 carbon atoms per alkyl group, α-, β- or γ-pyridyl, phenyl or phenoxy, it being possible for the aryl groups in turn to be substituted by trifluoromethyl, fluorine, chlorine, nitro, or alkyl or alkoxy each having 1 to 4 carbon atoms.

The compounds of the general formula (I) according to the invention can be prepared in various ways, depending on the nature of the substituents.

The reaction according to process A of 1,4-dihydropyridine derivatives of the formula (II)

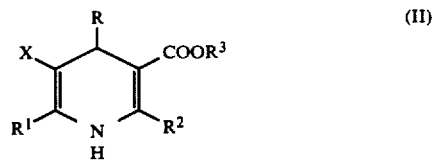

with oxidizing (dehydrogenating) agents proved to be particularly advantageous and of the widest applicability.

In the formula (II), the radicals R, R¹, R², R³ and X have the meaning indicated above.

1,4-Dihydropyridine derivatives of the formula (II) employed as starting material are known from the literature and can be prepared by methods known from the literature (see, for example, DOS (German Published Specification) No. 2,117,571, DOS (German Published Specification) No. 2,508,181 and U.S. application Ser. No. 83,844 filed 10/11/79, now pending.

Examples which may be mentioned are: 2-hydroxyethyl methyl 1,4-dihydro-2,6-dimethyl-4-(2-nitrophenyl)pyridine-3,5-dicarboxylate, 2-chloroethyl isopropyl 1,4-dihydro-2,6-dimethyl-4-(2-n-nitrophenyl)-pyridine-3,5-dicarboxylate, 2-cyanoethyl methyl 1,4-dihydro-2,6-dimethyl-4-(2-nitrophenyl)pyridine-3,5-dicarboxylate, 2-acetoxyethyl isopropyl 1,4-dihydro-2,6-dimethyl-4-(2-nitrophenyl)pyridine-3,5-dicarboxylate 2-acetoxyethyl methyl 1,4-dihydro-2,6-dimethyl-4-(3-nitrophenyl)pyridine-3,5-dicarboxylate, 2-phenoxyethyl ethyl 1.4-dihydro-2,6-dimethyl-4-(3-nitrophenyl)pyridine-3,5-dicarboxylate, 2-hydroxyethyl 2-N-benzyl-N-methylaminoethyl 1,4-dihydro-2,6-dimethyl-4-(3-nitrophenyl)pyridine-3,5-dicarboxylate, 3-hydroxypropyl isopropyl 1,4-dihydro-2,6-dimethyl-4-(3-nitrophenyl)pyridine-3,5-dicarboxylate, 2-hydroxyethyl 3-acetyl-1,4-dihydro-2,6-dimethyl-4-(3-nitrophenyl)-pyridine-5-carboxylate, 2-hydroxyethyl 3-acetyl-1,4-dihydro-2,6-dimethyl-4-(2-trifluoromethylphenyl)pyridine-5-carboxylate, 2-cyanoethyl 3-acetyl-1,4-dihydro-2,6-dimethyl-4-(2-trifluoromethylphenyl)-pyridine-5-carboxylate, 2-acetoxyethyl 3-acetyl-1.4-dihydro-2,6-dimethyl-4-(2-trifluoromethylphenyl)pyridine-5-carboxylate, 2-hydroxyethyl 3-cyano-1,4-dihydro-2,6-dimethyl-4-(3-nitrophenyl)pyridine-5-carboxylate, 2-hydroxyethyl 3-cyano-1,4-dihydro-2,6-dimethyl-4-(trifluoromethylphenyl)pyridine-5-carboxylate, 2-hydroxyethyl 3-cyano-1,4-dihydro-2,6-dimethyl-4-(2-methoxyphenyl)pyridine-5-carboxylate, 2-acetoxyethyl 3-cyano-1,4-dihydro-2,6-dimethyl-4-(2-chlorophenyl)-pyridine-5-carboxylate, 2-hydroxyethyl isopropyl 1,4-dihydro-2,6-dimethyl-4-(2-pyridyl)pyridine-3,5-dicarboxylate, 2-hydroxyethyl isopropyl 1,4-dihydro-2,6-dimethyl-4-(3-pyridyl)pyridine-3,5-dicarboxylate, 2-hydroxyethyl methyl 1,4-dihydro-2,6-dimethyl-4-(2,1,3-benzoxadiazol-4-yl)pyridine-3,5-dicarboxylate and 2- cyanoethyl isopropyl 1,4-dihydro-2,6-dimethyl-4-(2,1,3-benzoxadiazol-4-yl)pyridine-3,5-dicarboxylate.

The principal suitable oxidizing agents (dehydrogenating agents) are nitric acid or nitrous acid, chromium(VI) oxide or sodium dichromate, nitrogen oxides, chloranil, tetracyanobenzoquinone or anodic oxidation in the presence of a suitable electrolyte system, such as, for example, acetonitrile/lithium perchlorate.

The principal diluents which may be mentioned are water and all inert organic solvents. These preferably include benzene, toluene, acetonitrile, glacial acetic acid and hexamethylphosphoric acid triamide.

The reaction temperatures can be varied within a wide range. In general, the reaction is carried out between 0° and 200° C., preferably so that it can be well controlled.

Depending on the nature of the substituents, it can be advantageous not to undertake the conversion of the 1,4-dihydropyridine derivative of the general formula (II) into the compounds of the general formula (I) according to the invention as the last synthetic step.

Thus, according to process variant B, pyridinecarboxylic acids of the general formula (III)

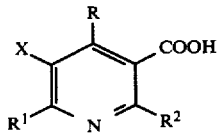

in which

R, R¹, R² and X have the meaning indicated above, can also be converted into the pyridinecarboxylic esters of the general formula (I) according to the invention by methods known from the literature. It is also possible to acylate the compounds of the general formula (VII) according to the invention

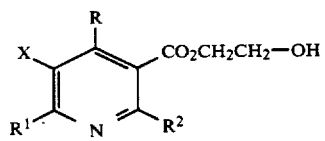

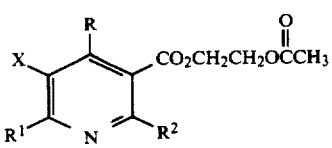

to give compounds of the general formula (VIII) according to the invention, R, R¹, R² and X having the meaning indicated above (see Example 4).

The foregoing preparation processes are only indicated for the purposes of elucidation, and the preparation of the compounds of the formula (I) is not restricted to these processes, but every modification of these processes can be used in the same manner for the preparation of the compounds according to the invention.

Depending on the choice of the substituents, the compounds according to the invention can exist in stereoisomeric forms, which are either related as image and mirror image (enantiomers) or which are not related as image and mirror image (diastereomers). The present invention relates not only to the antipodes and the racemic forms, but also to the mixtures of diastereomers.

The racemic forms can be separated into the homogeneous stereoisomeric components in a known manner, as can the diastereomers (compare, for example, E. L. Eliel, Stereochemistry of Carbon Compounds, McGraw Hill, (1962).

Apart from the preparation examples listed below, the following active compounds according to the invention may be mentioned: 2-hydroxyethyl methyl 2,6-dimethyl-4-(2-nitrophenyl)pyridine-3,5-dicarboxylate, 2-hydroxyethyl ethyl 2,6-dimethyl-4-(2-nitrophenyl)-pyridine-3,5-dicarboxylate, 2-hydroxyethyl isobutyl 2,6-dimethyl-4-(2-nitrophenyl)pyridine-3,5-dicarboxylate, 2-hydroxyethyl cyclopentyl 2,6-dimethyl-4-(2-nitrophenyl)pyridine-3,5-dicarboxylate, 3-hydroxypropyl isopropyl 2,6-dimethyl-4-(3-nitrophenyl)pyridine-3,5-dicarboxylate, 3-acetoxypropyl isopropyl 2,6-dimethyl-4-(3-nitrophenyl)pyridine-3,5-dicarboxylate, 3-chloropropyl isopropyl 2,6-dimethyl-4-(3-nitrophenyl)pyridine-3,5-dicarboxylate, 3-cyanopropyl isopropyl 2,6-dimethyl-4-(3-nitrophenyl)pyridine-3,5-dicarboxylate, 4-hydroxybutyl isopropyl 2,6-dimethyl-4-(3-nitrophenyl)pyridine-3,5-dicarboxylate, 2-hydroxyethyl benzyl 2,6-dimethyl-4-(3-nitrophenyl)pyridine-3,5-dicarboxylate, 2-hydroxyethyl 2,2,2-trifluoroethyl 2,6-dimethyl-4-(3-nitrophenyl)pyridine-3,5-dicarboxylate, 2-hydroxyethyl 2,6-dimethyl-4-(3-nitrophenyl)-3-acetylpyridine-5-carboxylate, 2-acetoxyethyl 2,6-dimethyl-4-(3-nitrophenyl)-3-acetylpyridine-5-carboxylate, 2-chloroethyl 2,6-dimethyl-4-(3-nitrophenyl)-3-acetylpyridine-5-carboxylate, 2-hydroxyethyl isopropyl 2,6-dimethyl-4-(2-chlorophenyl)pyridine-3,5-dicarboxylate, 2-hydroxyethyl isopropyl 2,6-dimethyl-4-(2,3-dichlorophenyl)pyridine-3,5-dicarboxylate, 2-hydroxyethyl methyl 2,6-dimethyl-4-(2,3-dichlorophenyl)pyridine-3,5-dicarboxylate, 2-hydroxyethyl isopropyl 2,6-dimethyl-4-(3-pyridyl)pyridine-3,5-dicarboxylate, 2-hydroxyethyl isopropyl 2,6-dimethyl-4-(2-pyridyl)pyridine-3,5-dicarboxylate, 2-hydroxyethyl isopropyl 2,6-dimethyl-4-(2-methylthio-3-pyridyl)pyridine-3,5-dicarboxylate, 2-hydroxyethyl isopropyl 2,6-dimethyl-4-(2,1,3-benzoxadiazo-4-yl)pyridine-3,5-dicarboxylate, 2-hydroxyethyl methyl 2,6-dimethyl-4-(2,1,3-benzoxadiazol-4-yl)pyridine-3,5-dicarboxylate, 3-(2-hydroxyethyl) 5-isopropyl 6-hydroxymethyl-2-methyl-4-(3-nitrophenyl)pyridine-3,5-dicarboxylate, 3-(2-cyanoethyl) 5-isopropyl 6-hydroxymethyl-2-methyl-4-(3-nitrophenyl)pyridine-3,5-dicarboxylate, 2-hydroxyethyl 5,7-dihydro-2-methyl-4-(2-nitrophenyl)-5-oxofuro[3,4-b]pyridine-3-carboxylate, 2-cyanoethyl 5,7-dihydro-2-methyl-4-(2-trifluoromethylphenyl)-5-oxofuro[3,4-b]pyridine-3-carboxylate and 2-acetoxyethyl 5,7-dihydro-2-methyl-4-(3-pyridyl)-5-oxofuro[3,4-b]-pyridine-3-carboxylate.

The compounds mentioned are particularly suitable for the treatment of hypoxic and/or ischaemic damage, principally of the central nervous system, and of sclerotic, necrotic or age-related cerebral insufficiency and psychopathological states.

The advantageous properties are demonstrated by the following investigations.

(a) Protective action against hypoxia in the model of hypoxia-induced retrograde amnesia in the passive avoidance test (Compare S. J. Sara and D Lefevre, Psychopharmakologia, 25, 32–40, 1972)

In a cage having light and dark sections, rats are trained, using an electroshock, to avoid the dark section of the cage. When the experimental animals are then exposed to a hypoxic atmosphere (3.5% by volume of O₂), the contents of the memory are retroactively destroyed. The abovementioned compounds antagonize retrograde amnesia completely.

(b) Increase in tolerance of hypoxia

Mice treated with substance or placebo are placed in a chamber through which a hypoxic gas mixture (3.5% by volume of O₂) is passed until 85% of the control animals are dead. The abovementioned compounds significantly increase the number of surviving animals.

(c) Inhibition of defensive behaviour

Mice, which have been kept isolated, show "aggressive-defensive behavior" on electrical provocation. The compounds according to the invention, which are otherwise without general sedative effects, completely inhibit this behavior.

The compounds mentioned have a strong protective action against hypoxia, although they affect neither the blood pressure nor the heart rate, nor are they vasoactive on isolated strips of rabbit vascular tissue. The psychotropic effect shown is of additional therapeutic significance, particularly in gerontology.

The new active compounds can be converted, in a known manner, into the customary formulations, such as tablets, capsules, coated tablets, pills, granules, aerosols, syrups, emulsions, suspensions and solutions, using inert, non-toxic pharmaceutically suitable vehicles or solvents. The therapeutically active compound desirably in each case, is present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example when using water as the diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid vehicles, such as, for example, natural rock powder (for example kaolins, aluminas, talc and chalk), synthetic rock powders (for example highly disperse silica, silicates), sugars (for example cane sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatin and the like. Furthermore, lubricants such as magnesium stearate, sodium lauryl sulphate and talc, can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.01 to 10 mg/kg, preferably about 0.1 to 5 mg/kg of body weight daily to achieve effective results; in the case of oral administration, the dose is about 0.05 to 20 mg/kg, preferably 0.5 to 5 mg/kg of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus it may suffice in some cases to manage with less than the abovementioned minimum amount while in other cases the upper limit mentioned must be exceeded. Where relatively large amounts are administered, it can be advisable to divide these into several individual administrations during the course of the day. The same dosage range is envisaged for administration in human medicine. In this connection, the above statements similarly apply.

PREPARATION EXAMPLES

Example 1

2-Hydroxyethyl isopropyl 2,6-dimethyl-4-(3-nitrophenyl)pyridine-3,5-dicarboxylate.

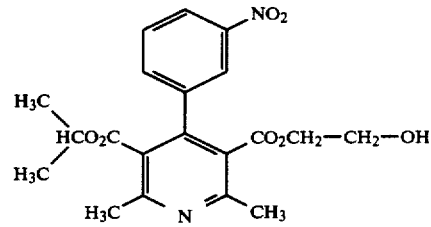

20 g (49.5 mmol) of 2-hydroxyethyl isopropyl 1,4-dihydro-2,6-dimethyl-4-(3-nitrophenyl)pyridine-3,5-dicarboxylate were introduced into a mixture of 83 ml of 96% strength nitric acid in 660 ml of water and heated to boiling for 1 hour. The mixture was then cooled down to 5° to 10° C. and made weakly alkaline with dilute sodium hydroxide solution. The oil which had separated out was extracted with methylene chloride, the extracts were dried over sodium sulphate and evaporated in vacuo. The oily residue was induced to crystallize by trituration with ether/petroleum ether, filtered off with suction and recrystallized from methanol.

Melting point: 120° C. yield: 13.1 g (66%)

Example 2

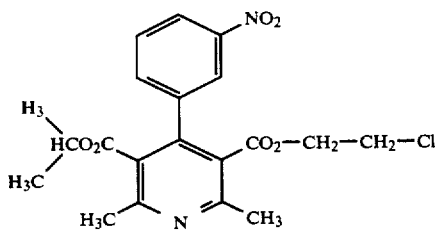

2-Chloroethyl isopropyl 2,6-dimethyl-4-(3-nitrophenyl)pyridine-3,5-dicarboxylate, of melting point 80° C., was obtained in analogy to Example 1 by reaction of 2-chloroethyl isopropyl 1,4-dihydro-2,6-dimethyl-4-(3-nitrophenyl)pyridine-3,5-dicarboxylate with nitric acid.

Yield: 69% of theory.

Example 3

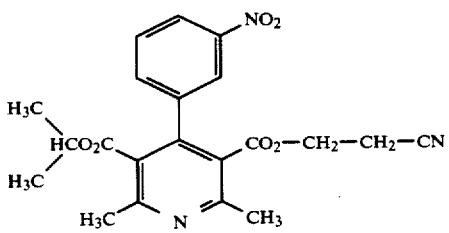

2-Cyanoethyl isopropyl 2,6-dimethyl-4-(3-nitrophenyl)pyridine-3,5-dicarboxylate, of melting point 93° C., was obtained in analogy to Example 1 by reaction of 2-cyanoethyl isopropyl 1,4-dihydro-2,6-dimethyl-4-(3-nitrophenyl)pyridine-3,5-dicarboxylate with nitric acid.

Yield: 71% of theory.

Example 4

2-Acetoxyethyl isopropyl 2,6-dimethyl-4-(3-nitrophenyl)pyridine-3,5-dicarboxylate

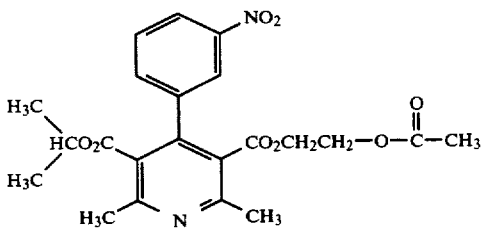

20.1 g (50 mmols) of 2-hydroxyethyl isopropyl 2,6-dimethyl-4-(3-nitrophenyl)pyridine-3,5-dicarboxylate (Example 1) were dissolved in 75 ml of pyridine. 5.9 g (75 mmols) of acetyl chloride were added to this. After the exothermic reaction was over, the reaction mixture was stirred at room temperature for 3 hours, poured into water and extracted with $CH_2Cl_2$. The organic extracts were washed with dilute hydrochloric acid and, after drying over sodium sulphate, evaporated in vacuo. The resulting oil crystallized completely, it was stirred with petroleum ether, filtered off with suction and dried.

Melting point 68° C., yield: 20.5 g (93%).

Example 5

Isopropyl 2-methoxyethyl 2,6-dimethyl-4-(3-nitrophenyl)-pyridine-3,5-dicarboxylate

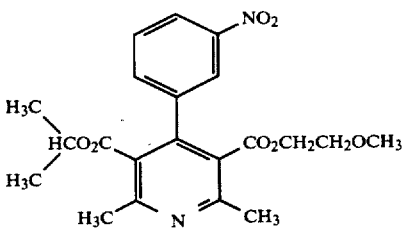

6.8 g of chromium(VI) oxide were added in portions in a boiling solution of 41.8 g (100 mmols) of isopropyl 2-methoxyethyl 1,4-dihydro-2,6-dimethyl-4-(3-nitrophenyl)pyridine-3,5-dicarboxylate in 160 ml of glacial acetic acid. The mixture was then heated under reflux for a further 30 minutes and, after cooling down, poured into ammoniacal ice-water. The mixture was extracted with chloroform and the extracts, after drying over sodium sulphate, were evaporated in vacuo. 35.9 g (86% of theory) of an oil resulted.

Example 6

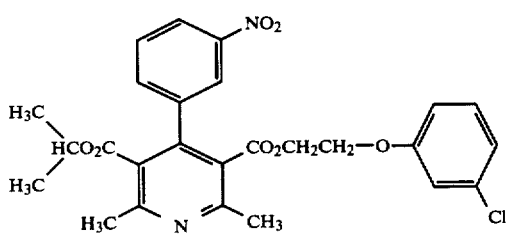

2-(3-Chlorophenoxy)ethyl isopropyl 2,6-dimethyl-4-(3-nitrophenyl)pyridine-3,5-dicarboxylate, of melting point 79° C., was obtained in analogy to Example 1 by reaction of 2-(3-chlorophenoxy)ethyl isopropyl 1,4-dihydro-2,6-dimethyl-4-(3-nitrophenyl)pyridine-3,5-dicarboxylate with nitric acid.

Yield: 85% of theory.

Example 7

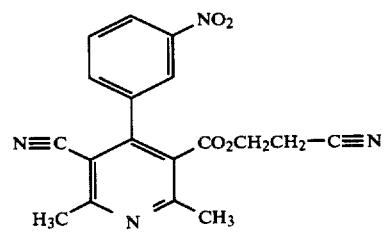

2-Cyanoethyl 3-cyano-2,6-dimethyl-4-(3-nitrophenyl)pyridine-5-carboxylate, of melting point 142° C., was obtained in analogy to Example 1 by reaction of 2-cyanoethyl 3-cyano-1,4-dihydro-2 6-dimethyl-4-(3-nitrophenyl)pyridine-5-carboxylate with nitric acid.

Yield: 69% of theory.

Example 8

2-Cyanoethyl 3-acetyl-2,6-dimethyl-4-(3-nitrophenyl)-pyridine-5-carboxylate

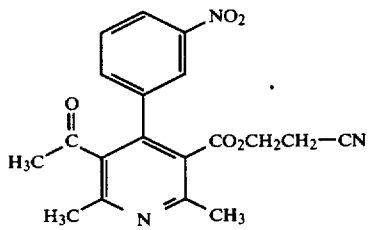

A solution of 10 g (27 mmols) of 2-cyanoethyl 3-acetyl-1,4-dihydro-2,6-dimethyl-4-(3-nitrophenyl)-pyridine-5-carboxylate in an electrolyte of 5 g of lithium perchlorate in 250 ml of acetonitrile was electrolyzed on a platinum anode. After passing through 2 Faraday equivalents, the electrolysis was stopped, the anolyte was evaporated in vacuo, the residue was taken up in sodium bicarbonate solution and extracted several times with methylene chloride. The organic extracts were washed with water, dried over sodium sulphate and then evaporated in vacuo. The resulting oil crystallized completely, and the solid product was thoroughly stirred in petroleum ether, filtered off with suction and dried, melting point 85° C., yield: 7.5 g (75%).

Example 9

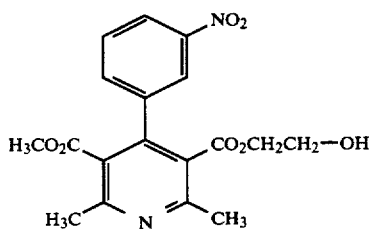

2-Hydroxyethyl methyl 2,6-dimethyl-4-(3-nitro phenyl)pyridine-3,5-dicarboxylate, of melting point 115° C., was obtained in analogy to Example 1 by reaction of 2-hydroxyethyl methyl 1,4-dihydro-2,6-dimethyl-4-(3-nitrophenyl)pyridine-3,5-dicarboxylate with nitric acid.
Yield: 59% of theory.

Example 10

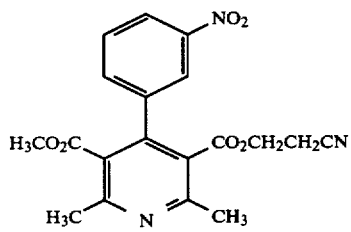

2-Cyanoethyl methyl 2,6-dimethyl-4-(3-nitrophenyl)-pyridine-3,5-dicarboxylate, of melting point 98° C., was obtained in analogy to Example 1 by reaction of 2-cyanoethyl methyl 1,4-dihydro-2,6-dimethyl-4-(3-nitrophenyl)pyridine-3,5-dicarboxylate with nitric acid.
Yield: 65% of theory.

Example 11

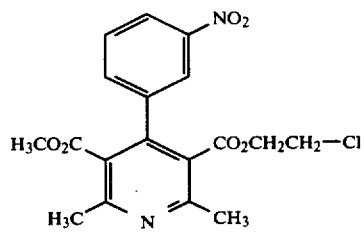

2-Chloroethyl methyl 2,6-dimethyl-4-(3-nitrophenyl)pyridine-3,5-dicarboxylate, of melting point 60° C., was obtained in analogy to Example 1 by reaction of 2-chloroethyl methyl 1,4-dihydro-2,6-dimethyl-4-(3-nitrophenyl)pyridine-3,5-dicarboxylate with nitric acid.
Yield: 55% of theory.

Example 12

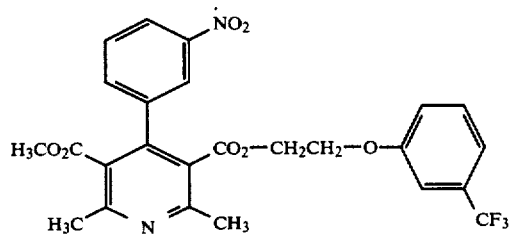

Methyl 2-(3-trifluoromethylphenoxy)ethyl 2,6-dimethyl-4-(3-nitrophenyl)pyridine-3,5-dicarboxylate, of melting point 88° C., was obtained in analogy to Example 1 by reaction of methyl 2-(3-trifluoromethylphenoxy)ethyl 1,4-dihydro-2,6-dimethyl-4-(3-nitrophenyl)pyridine-3,5-dicarboxylate with nitric acid.
Yield: 89% of theory.

Example 13

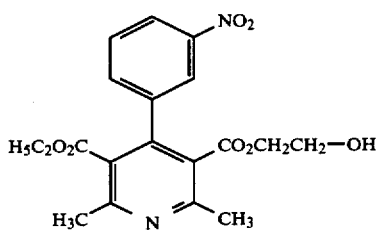

Ethyl 2-hydroxyethyl 2,6-dimethyl-4-(3-nitrophenyl)pyridine-3,5-dicarboxylate, of melting point 88° C., was obtained in analogy to Example 1 by reaction of ethyl 2-hydroxyethyl 1,4-dihydro-2,6-dimethyl-4-(3-nitrophenyl)pyridine-3,5-dicarboxylate with nitric acid.
Yield: 51% of theory.

Example 14

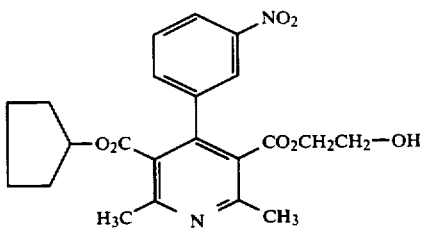

Cyclopentyl 2-hydroxyethyl 2,6-dimethyl-4-(3-nitrophenyl)pyridine-3,5-dicarboxylate, of melting point 112° C., was obtained in analogy to Example 1 by reaction of cyclopentyl 2-hydroxyethyl 1,4-dihydro-2,6-dimethyl-4-(3-nitrophenyl)pyridine-3,5-dicarboxylate with nitric acid.

Yield: 63% of theory.

Example 15

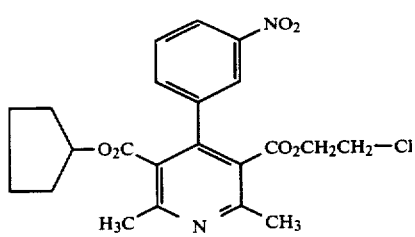

2-Chloroethyl cyclopentyl 2,6-dimethyl-4-(3-nitrophenyl)pyridine-3,5-dicarboxylate, of melting point 84° C., was obtained in analogy to Example 1 by reaction of 2-chloroethyl cyclopentyl 1,4-dihydro-2,6-dimethyl-4-(3-nitrophenyl)pyridine-3,5-dicarboxylate with nitric acid.

Yield. 71% of theory.

Example 16

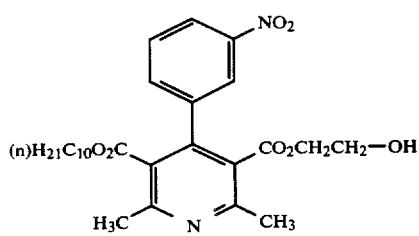

Decyl 2-hydroxyethyl 2,6-dimethyl-4-(3-nitrophenyl)pyridine-3,5-dicarboxylate, of melting point 60° C., was obtained in analogy to Example 1 by reaction of decyl 2-hydroxyethyl 1,4-dihydro-2,6-dimethyl-4-(3-nitrophenyl)pyridine-3,5-dicarboxylate with nitric acid.

Yield: 71% of theory.

Example 17

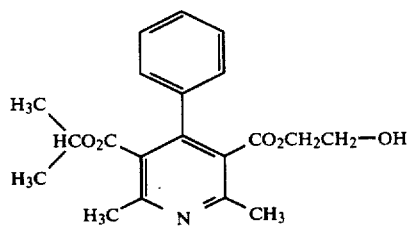

2-Hydroxyethyl isopropyl 2,6-dimethyl-4-phenylpyridine-3,5-dicarboxylate, of melting point 79° C., was obtained in analogy to Example 1 by reaction of 2-hydroxyethyl isopropyl 1,4-dihydro-2,6-dimethyl-4-phenylpyridine-3,5-dicarboxylate with nitric acid.

Yield: 82% of theory.

Example 18

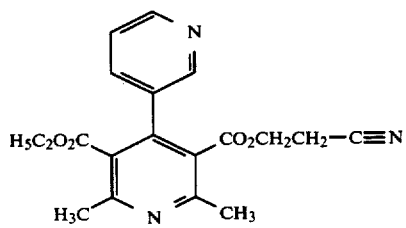

2-Cyanoethyl ethyl 2,6-dimethyl-4-(3-pyridyl)pyridine-3,5-dicarboxylate, of melting point 90° C., was obtained in analogy to Example 1 by reaction of 2-cyanoethyl ethyl 1,4-dihydro-2,6-dimethyl-4-(3-pyridyl)pyridine-3,5-dicarboxylate with nitric acid.

Yield 52% of theory.

Example 19

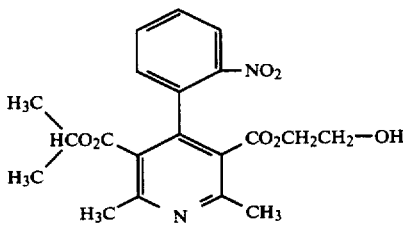

2-Hydroxyethyl isopropyl 2,6-dimethyl-4-(2-nitrophenyl)pyridine-3,5-dicarboxylate, of melting point 78° C., was obtained in analogy to Example 1 by reaction of 2-hydroxyethyl isopropyl 1,4-dihydro-2,6-dimethyl-4-(2-nitrophenyl)pyridine-3,5-dicarboxylate with nitric acid.

Yield 83% of theory

Example 20

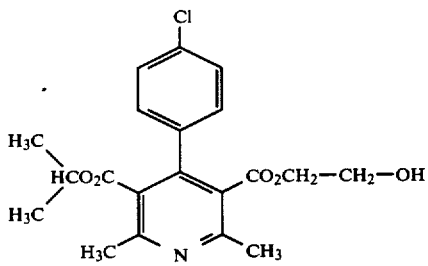

2-Hydroxyethyl-isopropyl 2,6-dimethyl-4-(4-chlorophenyl)pyridine-3,5-dicarboxylate, of melting point 120° C., was obtained in analogy to Example 1 by reaction of 2-hydroxyethyl isopropyl 1,4-dihydro-2,6-dimethyl-4-(4-chlorophenyl)pyridine-3,5-dicarboxylate with nitric acid.

Yield 88% of theory.

Example 21

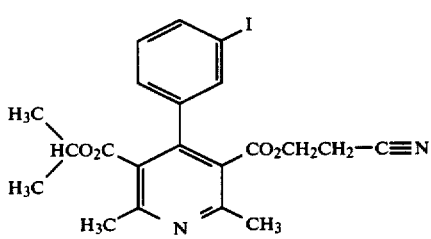

2-Cyanoethyl isopropyl 2,6-dimethyl-4-(3-iodophenyl)pyridine-3,5-dicarboxylate, of melting point 69° C., was obtained in analogy to Example 1 by reaction of 2-cyanoethyl isopropyl 1,4-dihydro-2,6-dimethyl-4-(3-iodophenyl)pyridine-3,5-dicarboxylate with nitric acid.

Yield 75% of theory.

Example 22

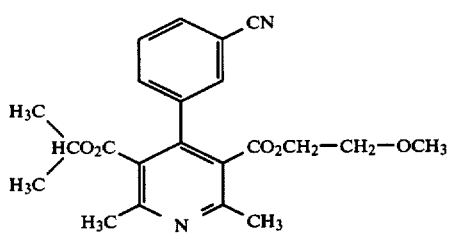

Isopropyl 2-methoxyethyl 2,6-dimethyl-4-(3-cyanophenyl)pyridine-3,5-dicarboxylate, of melting point 50° C., was obtained in analogy to Example 1 by reaction of isopropyl 2-methoxyethyl 1,4-dihydro-2,6-dimethyl-4-(3-cyanophenyl)pyridine-3,5-dicarboxylate with nitric acid.

Yield 73% of theory

Example 23

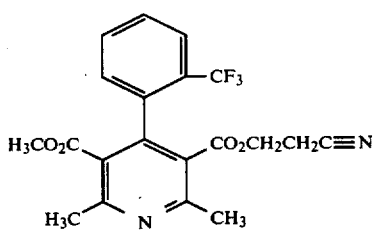

2-Cyanoethyl methyl 2,6-dimethyl-4-(2-trifluoromethylphenyl)pyridine-3,5-dicarboxylate, of melting point 74° C., was obtained in analogy to Example 1 by reaction of 2-cyanoethyl methyl 1,4-dihydro-2,6-dimethyl-4-(2-trifluoromethylphenyl)pyridine-3,5-dicarboxylate with nitric acid.

Yield 85% of theory

Example 24

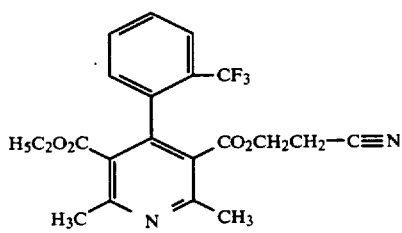

2-Cyanoethyl ethyl 2,6-dimethyl-4-(2-trifluoromethylphenyl)pyridine-3,5-dicarboxylate, of melting point 68° C., was obtained in analogy to Example 1 by reaction of 2-cyanoethyl ethyl 1,4-dihydro-2,6-dimethyl-4-(2-trifluoromethylphenyl)pyridine-3,5-dicarboxylate with nitric acid.

Yield 69% of theory.

Example 25

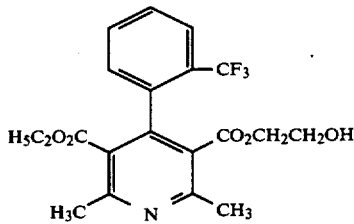

Ethyl 2-hydroxyethyl 2,6-dimethyl-4-(2-trifluoromethylphenyl)pyridine-3,5-dicarboxylate, of melting point 86° C., was obtained in analogy to Example 1 by reaction of ethyl 2-hydroxyethyl 1,4-dihydro-2,6-dimethyl-4-(2-trifluoromethylphenyl)pyridine-3,5-dicarboxylate with nitric acid.

Yield 75% of theory

Example 26

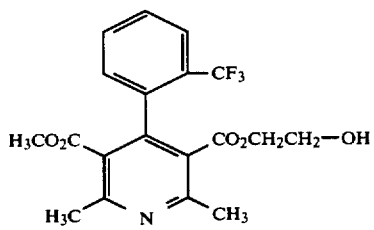

2-Hydroxyethyl methyl 2,6-dimethyl-4-(2-trifluoromethylphenyl)pyridine-3,5-dicarboxylate, of melting point 75° C., was obtained in analogy to Example 1 by reaction of 2-hydroxyethyl methyl 1,4-dihydro-2,6-dimethyl-4-(2-trifluoromethylphenyl)pyridine-3,5-dicarboxylate with nitric acid.

Example 27

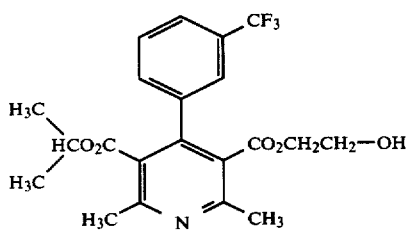

2-Hydroxyethyl isopropyl 2,6-dimethyl-4-(2-trifluoromethylphenyl)pyridine-3,5-dicarboxylate, of melting point 83° C., was obtained in analogy to Example 1 by reaction of 2-hydroxyethyl isopropyl 1 4-dihydro-2,6-dimethyl-4-(2-trifluoromethylphenyl)pyridine-3,5-dicarboxylate with nitric acid.

Yield 51% of theory.

Example 28

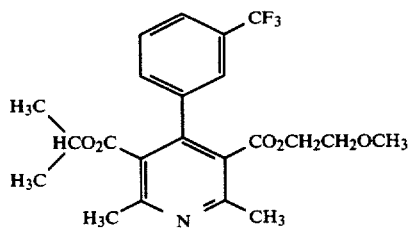

Isopropyl 2-methoxyethyl 2,6-dimethyl-4-(3-trifluoromethylphenyl)pyridine-3,5-dicarboxylate, of melting point 51° C., was obtained in analogy of Example 1 by reaction of isopropyl 2-methoxyethyl 1,4-dihydro-2,6-dimethyl-4-(3-trifluoromethylphenyl)pyridine-3,5-dicarboxylate with nitric acid.

Yield 65% of theory.

Example 29

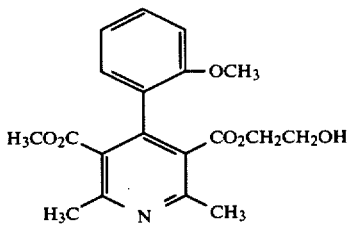

2-Hydroxyethyl methyl 2,6-dimethyl-4-(2-methoxyphenyl)pyridine-3,5-dicarboxylate, of melting point 90° C., was obtained in analogy to Example 1 by reaction of 2-hydroxyethyl methyl 1,4-dihydro-2,6-dimethyl-4-(2-methoxyphenyl)pyridine-3,5-dicarboxylate with nitric acid.

Yield 84% of theory.

Example 30

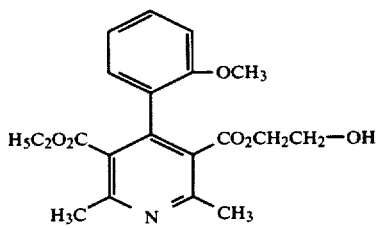

Ethyl 2-hydroxyethyl 2,6-dimethyl-4-(2-methoxyphenyl)pyridine-3,5-dicarboxylate, of melting point 95° C., was obtained in analogy to Example 1 by reaction of ethyl 2-hydroxyethyl 1,4-dihydro-2,6-dimethyl-4-(2-methoxyphenyl)pyridine-3,5-dicarboxylate with nitric acid.

Yield 71% of theory.

Example 31

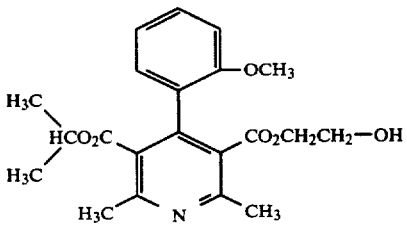

2-Hydroxyethyl isopropyl 2,6-dimethyl-4-(2-methoxyphenyl)pyridine-3,5-dicarboxylate, of melting point 68° C., was obtained in analogy to Example 1 by reaction of 2-hydroxyethyl isopropyl 1,4-dihydro-2,6-dimethyl-4-(2-methoxyphenyl)pyridine-3,5-dicarboxylate with nitric acid.

Yield 85% of theory.

Example 32

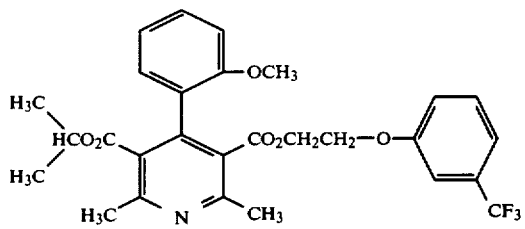

Isopropyl 2-(3-trifluoromethylphenoxy)ethyl 2,6-dimethyl-4-(2-methoxyphenyl)pyridine-3,5-dicarboxylate, of melting point 80° C., was obtained in analogy to Example 1 by reaction of isopropyl 2-(3-trifluoromethylphenoxy)ethyl 1,4-dihydro-2,6-dimethyl-4-(2-methoxyphenyl)pyridine-3,5-dicarboxylate with nitric acid.

Yield 65% of theory.

Example 33

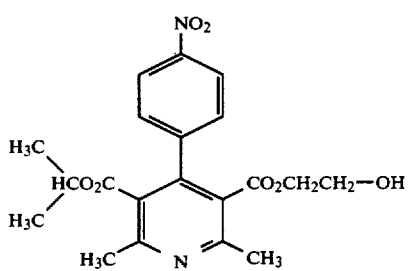

2-Hydroxyethyl isopropyl 2,6-dimethyl-4-(4-nitrophenyl)pyridine-3,5-dicarboxylate of melting point 145° C., was obtained in analogy to Example 1 by reaction of 2-hydroxyethyl isopropyl 1,4-dihydro-2,6-dimethyl-4-(4-nitrophenyl)pyridine-3,5-dicarboxylate with nitric acid.

Yield 62% of theory.

Example 34

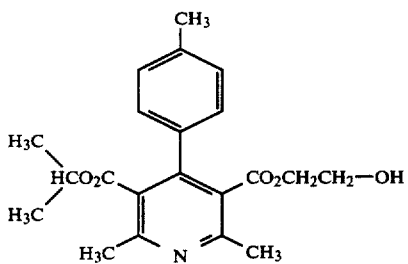

2-Hydroxyethyl isopropyl 2,6-dimethyl-4-(4-methylphenyl)pyridine-3,5-dicarboxylate, of melting point 72° C., was obtained in analogy to Example 1 by reaction of 2-hydroxyethyl isopropyl 1,4-dihydro-2,6-dimethyl-4-(4-methylphenyl)pyridine-3,5-dicarboxylate with nitric acid;

yield: 56% of theory.

Example 35

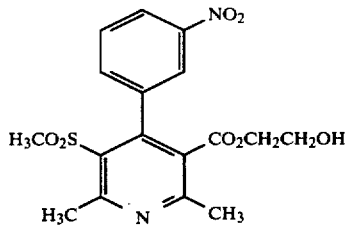

2-Hydroxyethyl 2,6-dimethyl-3-methylsulphonyl-4-(3-nitrophenyl)pyridine-5-carboxylate of melting point 120° C., was obtained in analogy to Example 1 by reaction of 2-hydroxyethyl 1,4-dihydro-2,6-dimethyl-3-methylsulphonyl-4-(3-nitrophenyl)pyridine-5-carboxylate with nitric acid.

Yield 53% of theory.

Example 36

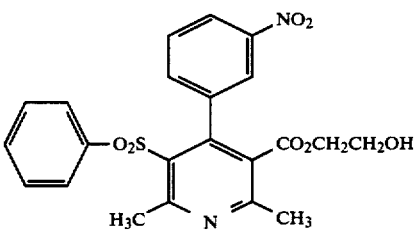

2-Hydroxyethyl 2,6-dimethyl-4-(3-nitrophenyl)-3-phenylsulphonylpyridine-5-carboxylate, of melting point 150° C., was obtained in analogy to Example 1 by reaction of 2-hydroxyethyl 1,4-dihydro-2,6-dimethyl-4-(3-nitrophenyl)-3-phenylsulphonylpyridine-5-carboxylate with nitric acid.

Yield 41% of theory

Example 37

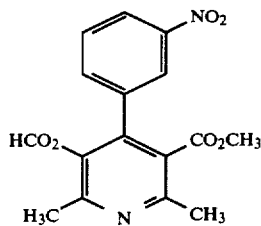

2,6-Dimethyl-4-(3-nitrophenyl)pyridine-3,5-dicarboxylic acid monomethyl ester, of melting point 202° C., was obtained in analogy to Example 11 by reaction of dimethyl 2,6-dimethyl-4-(3-nitrophenyl)pyridine-3,5-dicarboxylate with methanolic potassium hydroxide solution.

Yield 65% of theory.

Example 38

Potassium salt of 2-hydroxymethyl-6-methyl-4-(3-nitrophenyl)pyridine-3,5-dicarboxylic acid 5-(2-hydroxyethyl) ester.

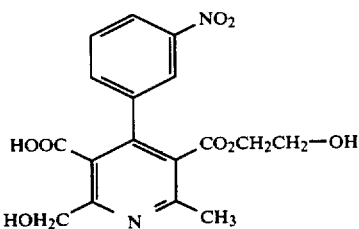

24 g (50 mmols) of 5-(2-acetoxyethyl) 3-ethyl 2-acetoxymethyl-6-methyl-4-(3-nitrophenyl)pyridine-3,5-dicarboxylate were dissolved in 120 ml of 1,2-dimethoxyethane and, after careful addition of a solution of 6.2 g of potassium hydroxide in 120 ml of water, was stirred at room temperature for two hours. The mixture was then extracted several times with methylene chloride, the aqueous phase was evaporated to dryness in vacuo and the residue was recrystallized from isopropanol.

Melting point 223° C. Yield 3.6 g (17% of theory).

Example 39

2-Hydroxyethyl 5,7-dihydro-2-methyl-4-(3-nitrophenyl)-5-oxofuro[3,4-b]pyridine-3-carboxylate

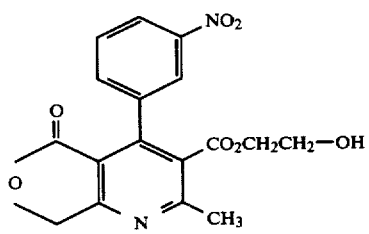

4 g of potassium salt of 2-hydroxymethyl-6-methyl-4-(3-nitrophenyl)pyridine-3,5-dicarboxylic acid 5-(2-hydroxyethyl) ester (Example 38) were dissolved in 4 ml of water and acidified with concentrated hydrochloric acid. After standing overnight at room temperature, the mixture was diluted with water, the oil which separated out was extracted with methylene chloride, the organic extracts, after drying over sodium sulphate, were evaporated in vacuo and the residue was recrystallized from isopropanol, melting point 130° C.

Yield: 2.3 g (64% of theory).

It will be appreciated that the instant specification and examples are set forth by way of illustration and not limitation, and that various modifications and changes may be made without departing from the spirit and scope of the present invention.

What is claimed is:

1. A composition for controlling disorders which are due to ischaemia and/or hypoxia comprising an ischaemia- and/or a hypoxia-controlling effective amount of a pyridine-carboxylic acid ester of the formula

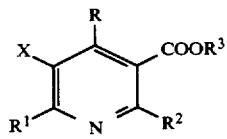

or a pharmaceutically acceptable salt thereof, in which
R represents a phenyl radical optionally containing 1 to 2 identical or different substituents from the group consisting of halogen, cyano, trifluoromethyl, alkyl having 1 to 4 carbon atoms and alkoxy having 1 to 4 carbon atoms, or represents pyridyl, $R^1$ represents alkyl having 1 to 4 carbon atoms, or hydroxyalkyl having 1 to 4 carbon atoms, $R^2$ represents alkyl having 1 to 4 carbon atoms, X represents the group —$COOR^5$, $R^5$ represents a straight chain, branched or cyclic alkyl radical having up to 12 carbon atoms which is optionally interrupted by 1 oxygen atom in the chain, and $R^3$ is always different from $R^5$ and represents alkyl with 1 to 4 carbon atoms substituted by hydroxy, alkoxy with 1 to 4 carbon atoms, cyano, halogen, trifluoromethylphenoxy, halogenphenoxy, or alkanoyloxy with 2 to 5 carbon atoms, or $R^1$ and X together form a 5- to 7-membered lactone ring, and a diluent.

2. A composition according to claim 1, in which $R^1$ together with X forms an oxofuro ring.

3. A composition according to claim 1, in which X is $COOR^5$.

4. A composition according to claim 1, wherein such pyridinecarboxylic acid ester is 2-cyanoethyl ethyl 2,6-dimethyl-4-(2-trifluoromethylphenyl)pyridine-3,5-dicarboxylate of the formula

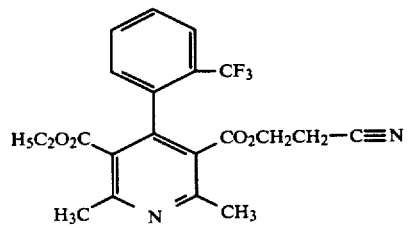

or a pharmaceutically acceptable salt thereof.

5. A composition according to claim 1, in the form of a tablet, capsule or pill containing a unit dose.

6. A composition for controlling disorders which are due to ischaemia and/or hypoxia comprising an ischaemia- and/or a hypoxia-controlling effective amount of a pyridinecarboxylic acid ester selected from the group consisting of 2-hydroxyethyl isopropyl 2,6-dimethyl-4-(3-nitrophenyl)-pyridine-3,5-dicarboxylate, 2-hydroxyethyl methyl 2,6-dimethyl-4-(3-nitrophenyl)pyridine-3,5-dicarboxylate, 2-cyanoethyl methyl 2,6-dimethyl-4-(3-nitrophenyl)-pyridine-3,5-dicarboxylate, methyl 2-(3-trifluoromethylphenoxy)ethyl 2,6-dimethyl-4-(3-nitrophenyl)pyridine-3,5-dicarboxylate, 2-hydroxyethyl 5,7-dihydro-2-methyl-4-(3-nitrophenyl)-5-oxofuro[3,4-b]pyridine-3-carboxylate, or a pharmaceutically acceptable salt thereof and a diluent.

7. A composition according to claim 6, wherein such compound is 2-hydroxyethyl isopropyl 2,6-dimethyl-4-(3-nitrophenyl)-pyridine-3,5-dicarboxylate of the formula

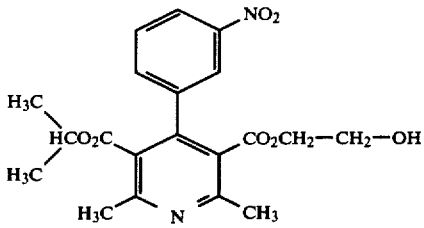

or a pharmaceutically acceptable salt thereof.

8. A composition according to claim 6, wherein such compound is 2-hydroxyethyl methyl 2,6-dimethyl-4-(3-nitro phenyl)pyridine-3,5-dicarboxylate of the formula

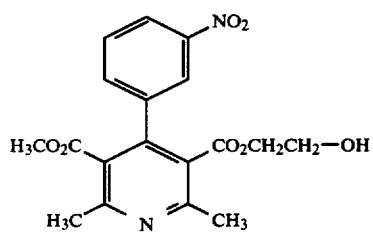

or a pharmaceutically acceptable salt thereof.

9. A composition according to claim 6, wherein such compound is 2-cyanoethyl methyl 2,6-dimethyl-4-(3-nitrophenyl)pyridine-3,5-dicarboxylate of the formula

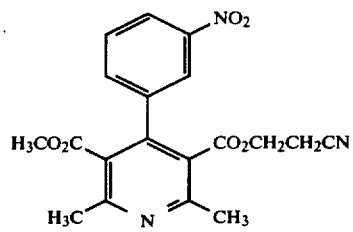

or a pharmaceutically acceptable salt thereof.

10. A composition according to claim 6, wherein such compound is methyl 2-(3-trifluoromethylphenoxy)ethyl 2,6-dimethyl-4-(3-nitrophenyl)pyridine-3,5-dicarboxylate of the formula

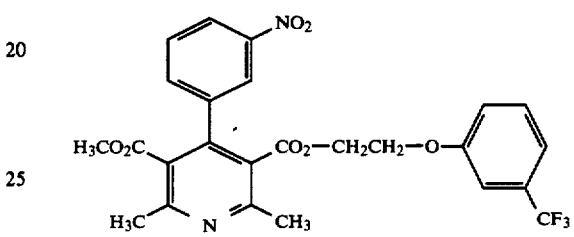

or a pharmaceutically acceptable salt thereof.

11. A composition according to claim 6, wherein such compound is 2-hydroxyethyl 5,7-dihydro-2-methyl-4-(3-nitrophenyl)-5-oxofuro[3,4-b]pyridine-3-carboxylate of the formula

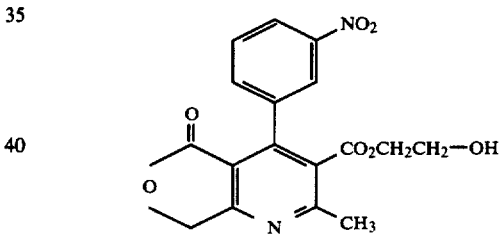

or a pharmaceutically acceptable salt thereof.

12. A composition according to claim 6, in the form of a tablet, capsule or pill containing a unit dose.

* * * * *

UNITED STATES PATENT AND TRADEMARK OFFICE
CERTIFICATE OF CORRECTION

PATENT NO. : 4,705,794
DATED : November 10, 1987
INVENTOR(S) : Egbert Wehinger, et al.

It is certified that error appears in the above-identified patent and that said Letters Patent is hereby corrected as shown below:

Title Page, under "Other Publications", line 8 — Delete "Vol. 17" and substitute --Vol. 7--

Col. 2, line 39 — Delete "exhibits" and substitute --exhibit--

Col. 2, line 66 — Delete "020" and substitute --O--

Col. 4, line 60 — Before "substituted" delete "by" and substitute --be--

Col. 5, line 29 — Delete "haveing" and substitute --having--

Col. 6, line 36 — After "(2-" delete "n-"

Col. 11, Example 2, left of formula — Delete "$H_3$" and substitute --$H_3C$--

Col. 19, Example 27, line 27 — Upper right of formula delete "$CF_3$" and substitute --$CF_3$--

Col. 19, line 62 — After "analogy" delete "of" and substitute --to--

Signed and Sealed this

Fifth Day of July, 1988

Attest:

DONALD J. QUIGG

Attesting Officer

Commissioner of Patents and Trademarks